United States Patent
Wu et al.

(10) Patent No.: US 10,203,243 B1
(45) Date of Patent: Feb. 12, 2019

(54) COMPRESSION AND FEATURE EXTRACTION FROM FULL WAVEFORM ULTRASOUND DATA

(71) Applicant: THE BOEING COMPANY, Chicago, IL (US)

(72) Inventors: Yuan-Jye Wu, Issaquah, WA (US); Hong H. Tat, Redmond, WA (US)

(73) Assignee: The Boeing Company, Chicago, IL (US)

(*) Notice: Subject to any disclaimer, the term of this patent is extended or adjusted under 35 U.S.C. 154(b) by 589 days.

(21) Appl. No.: 13/660,420

(22) Filed: Oct. 25, 2012

(51) Int. Cl.
*G03B 42/06* (2006.01)
*G01H 3/12* (2006.01)
*G01S 15/89* (2006.01)
*G01H 9/00* (2006.01)

(52) U.S. Cl.
CPC .............. *G01H 3/125* (2013.01); *G01H 9/002* (2013.01); *G01S 15/8915* (2013.01)

(58) Field of Classification Search
USPC .......................................................... 367/7
See application file for complete search history.

(56) References Cited

U.S. PATENT DOCUMENTS

| | | | | |
|---|---|---|---|---|
| 4,622,634 A | * | 11/1986 | Fidel | G01S 7/52028 600/437 |
| 4,865,040 A | * | 9/1989 | Ogasawara | G01S 7/52055 600/437 |
| 6,125,705 A | * | 10/2000 | Johnson | B23K 31/12 73/598 |
| 6,701,341 B1 | * | 3/2004 | Wu | A61B 5/0456 128/915 |
| 6,748,992 B1 | * | 6/2004 | Neubauer | B23K 20/10 156/378 |
| 8,525,835 B1 | | 9/2013 | Wu et al. | |

(Continued)

FOREIGN PATENT DOCUMENTS

| | | | | |
|---|---|---|---|---|
| EP | 1041396 A2 | * | 10/2000 | G01S 7/52034 |
| JP | 08103445 A | * | 4/1996 | |
| JP | 2005081082 A | * | 3/2005 | |

OTHER PUBLICATIONS

Lee, Daniel D., and H. Sebastian Seung. "Algorithms for non-negative matrix factorization." Advances in neural information processing systems. 2001.*

(Continued)

*Primary Examiner* — Isam A Alsomiri
*Assistant Examiner* — Jonathan D Armstrong
(74) *Attorney, Agent, or Firm* — Haynes and Boone, LLP

(57) ABSTRACT

The present disclosure provides a system, method, and apparatus for compressing and extracting features. The method involves transmitting at least one ultrasound signal into an object at a plurality of different locations on the object. Each of the locations is denoted by an x location and a y location. The method further involves receiving at least one waveform response signal. Also, the method involves generating a three-dimensional (3D) data cube with an X dimension, a Y dimension, and a time dimension. At least one waveform response signal is stored within the 3D data cube at the x location and the y location that is associated with the waveform response signal(s). Further, the method involves transforming at least one waveform response signal of the 3D data cube to produce at least one transformed signal.

21 Claims, 3 Drawing Sheets

Observed Signal = $\int \psi \otimes$ Echoes + noise = $A_1 \psi(t + t_1) + A_2 \psi(t + t_2) + \ldots +$ noise
where $\psi$ is the pulse from the transducer
$A_1, A_2$ are amplitudes of echoes
$t_1, t_2 \ldots$ are the times when the echoes occur.

(56) References Cited

U.S. PATENT DOCUMENTS

| | | | | |
|---|---|---|---|---|
| 2001/0052264 | A1* | 12/2001 | Johnson | B23K 31/125 |
| | | | | 73/628 |
| 2009/0324039 | A1* | 12/2009 | Miyaguchi | G06T 3/00 |
| | | | | 382/131 |
| 2014/0135623 | A1* | 5/2014 | Manak | A61B 8/4416 |
| | | | | 600/427 |
| 2014/0208850 | A1* | 7/2014 | Kim | G01N 29/14 |
| | | | | 73/587 |
| 2017/0045352 | A1* | 2/2017 | Colle | G01B 21/14 |
| 2017/0086798 | A1* | 3/2017 | Bjaerum | A61B 8/565 |
| 2017/0182605 | A1* | 6/2017 | Rajagopalan | B23K 37/053 |
| 2018/0008231 | A1* | 1/2018 | Miyake | A61B 8/14 |

OTHER PUBLICATIONS

Ermolov, I. N. "Progress in the theory of ultrasonic flaw detection. Problems and prospects." Russian Journal of Nondestructive Testing 40.10 (2004): 655-678.*

Abbate, Agostino, et al. "Signal detection and noise suppression using a wavelet transform signal processor: application to ultrasonic flaw detection." Ultrasonics, Ferroelectrics, and Frequency Control, IEEE Transactions on 44.1 (1997): 14-26.*

Lee, Daniel D., and H. Sebastian Seung. "Learning the parts of objects by non-negative matrix factorization." Nature 401.6755 (1999): 788-791.*

Feng, Tao, et al. "Local non-negative matrix factorization as a visual representation." Development and Learning, 2002. Proceedings. The 2nd International Conference on. IEEE, 2002.*

Prada, Claire, et al. "Time reversal techniques in ultrasonic nondestructive testing of scattering media." Inverse Problems 18.6 (2002): 1761.*

Shashua, Amnon, and Tamir Hazan. "Non-negative tensor factorization with applications to statistics and computer vision." Proceedings of the 22nd international conference on Machine learning. ACM, 2005.*

Shi, Guangming, et al. "Signal matching wavelet for ultrasonic flaw detection in high background noise." Ultrasonics, Ferroelectrics, and Frequency Control, IEEE Transactions on 58.4 (2011): 776-787.*

Hazan, Tamir, Simon Polak, and Amnon Shashua. "Sparse image coding using a 3D non-negative tensor factorization." Tenth IEEE International Conference on Computer Vision (ICCV'05) vol. 1. vol. 1. IEEE, 2005.*

Scikits-learn. 4.4. Decomposing signals in components (matrix factorization problems). URL: [http://scikit-learn.org/stable/modules/decomposition.html]. 2011.*

Yu, Shipeng, Jinbo Bi, and Jieping Ye. "Matrix-variate and higher-order probabilistic projections." Data Mining and Knowledge . Discovery 22.3 (2011): 372-392.*

Kohl, Christoph, and Doreen Streicher. "Results of reconstructed and fused NDT-data measured in the laboratory and on-site at bridges." Cement and Concrete Composites 28.4 (2006): 402-413.*

Missaoui, Rokia, et al. "A probabilistic model for data cube compression and query approximation." (2007).*

Anastassopoulos, A. A., V. N. Nikolaidis, and T. P. Philippidis. "A comparative study of pattern recognition algorithms for classification of ultrasonic signals." Neural Computing & Applications 8.1 (1999): 53-66.*

Sohn, Hoon, et al. "A review of structural health monitoring literature: 1996-2001." Los Alamos National Laboratory (2002).*

Zhuang, Xiaoyan, et al. "Ultrasonic signal compressive detection with sub-Nyquist sampling rate." (2012). Journal of Scientific & Industrial Research. vol. 71, Mar. 2012, pp. 195-199.*

Zhang, et al., "Contemporary Ultrasonic Signal Processing Approaches for Nondestructive Evaluation of Multilayered Structures", Nondestructive Testing and Evaluation, available online Jul. 13, 2011.

Lines, et al., "Rapid Distributed Data Collection and Processing with Arrays—The Next Step Beyond Full Waveform Capture", 9th Joint FAA/DoD/NASA Aging Aircraft Conference, Mar. 6-9, 2006.

Nikic, et al., "Compression of Hyperspectral and LiDAR Data using Implicit Geometry (IG) and Sub-space Representation Methods, Final Report on Methods and Algorithms (A004), Contract # HM1582-10-C-0011", Aug. 23, 2011.

Zhang, et al. "Reconstructing and Segmenting Hyperspectral Images from Compressed Measurements", 3rd Workshop on Hyperspectral Imaging and Signal Processing: Evolution in Remote Sensing (WHISPERS), Jun. 6-9, 2011.

* cited by examiner

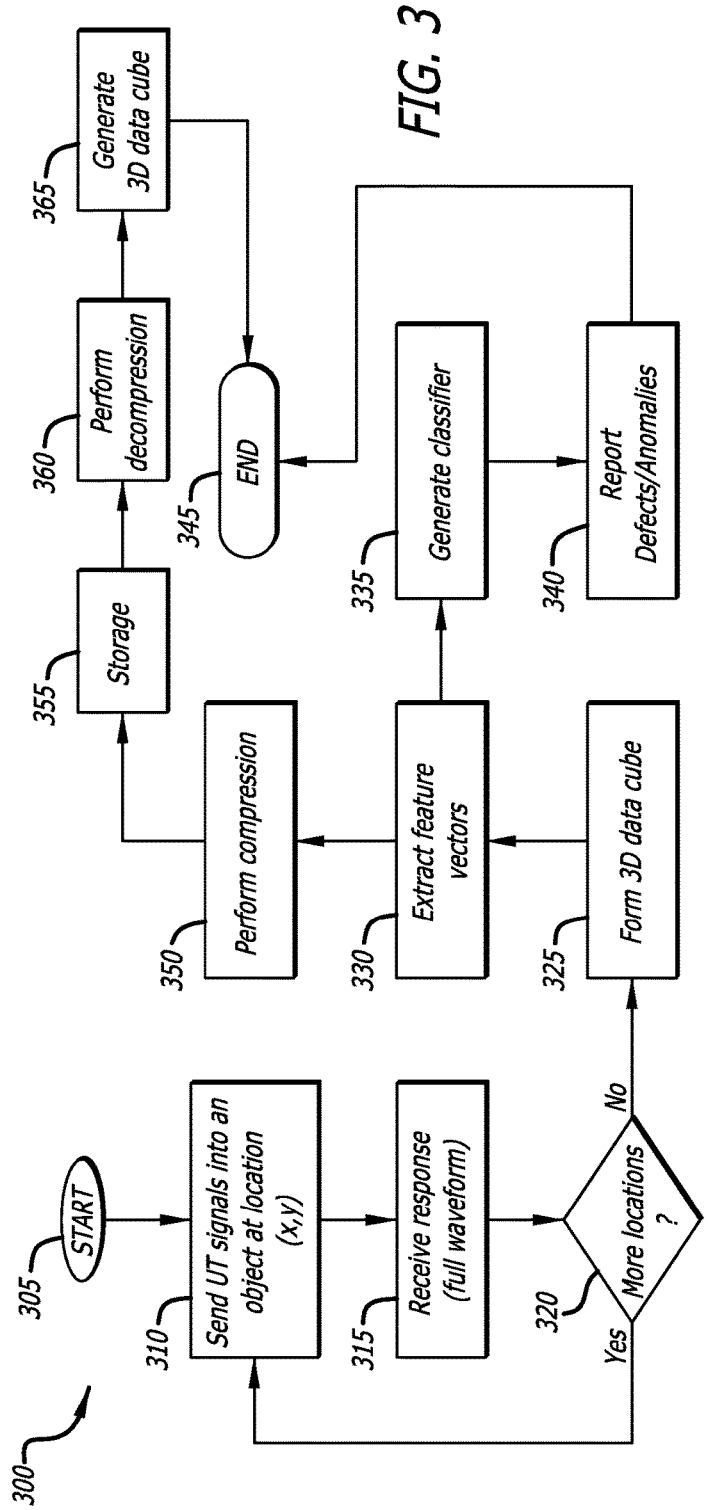

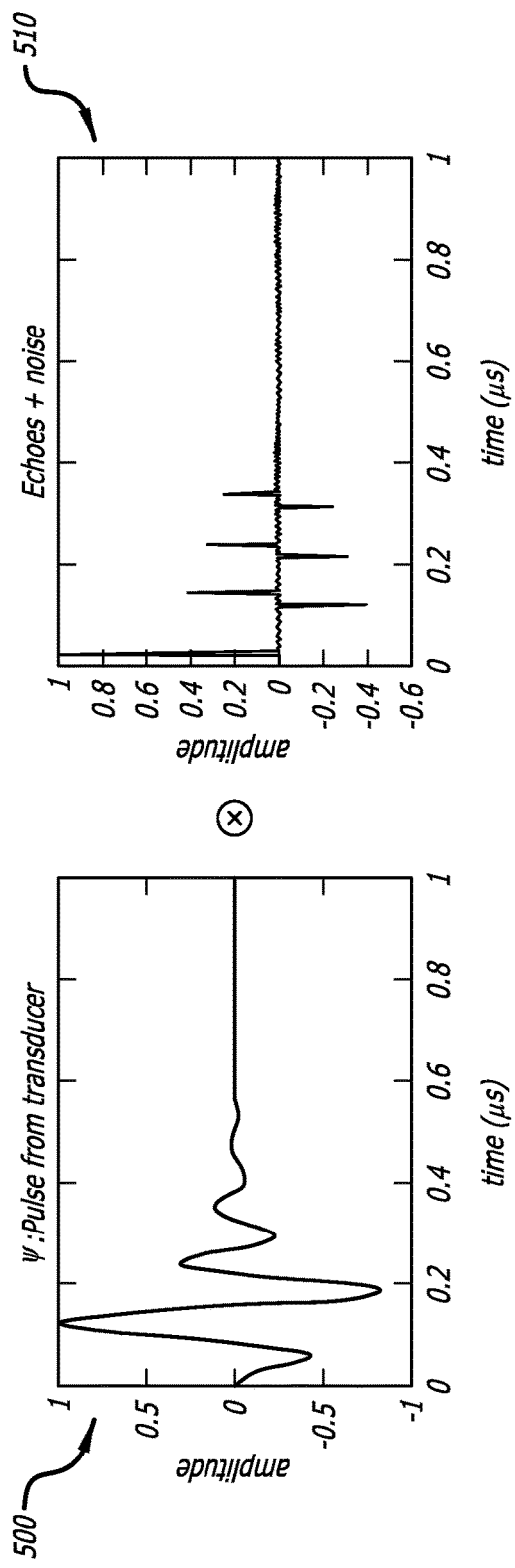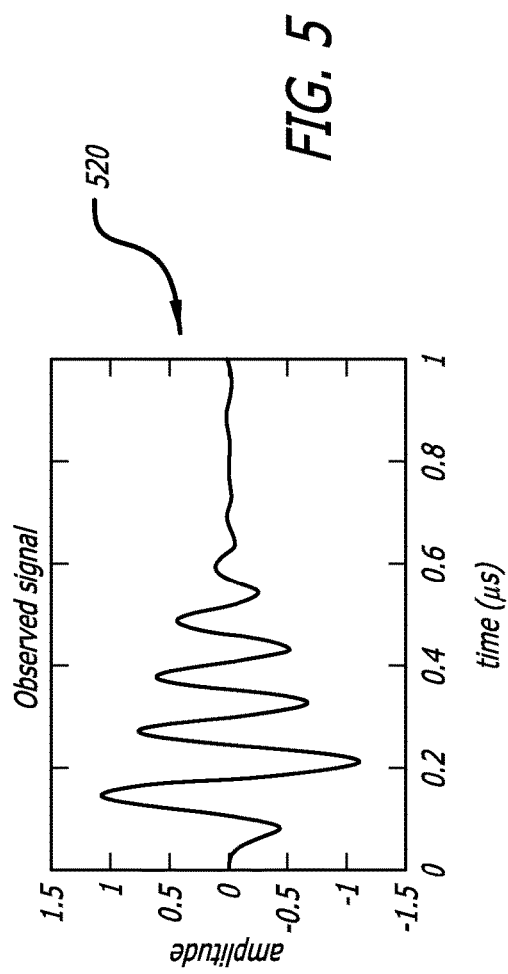
FIG. 5

COMPRESSION AND FEATURE EXTRACTION FROM FULL WAVEFORM ULTRASOUND DATA

BACKGROUND

The present disclosure relates to compression and feature extraction. In particular, it relates to compression and feature extraction from full waveform ultrasound data.

SUMMARY

The present disclosure relates to a method, system, and apparatus for compression and feature extraction from full waveform ultrasound data. The compression and feature extraction from full waveform ultrasound data may be used to perform scans of materials, such as composites for aircraft. In one or more embodiments, the present disclosure teaches a method for compressing and extracting features involving transmitting, by a transducer, at least one ultrasound signal into an object at a plurality of different locations on the object. In one or more embodiments, each of the plurality of different locations is denoted by an x location and a y location. The method further involves receiving, by a receiver, at least one waveform response signal. Also, the method involves generating, with at least one processor, a three-dimensional (3D) data cube with an X dimension, a Y dimension, and a time dimension. In at least one embodiment, at least one waveform response signal is stored within the 3D data cube at the x location and the y location associated with the waveform response signal(s). Further, the method involves transforming, with at least one processor, at least one waveform response signal of the 3D data cube to produce at least one transformed signal.

In one or more embodiments, at least one processor, for the transforming of the at least one waveform response signal, uses non-negative matrix factorization (NMF), total variation (TV), compressed sensing, and/or a method for deconvolution. In at least one embodiment, the method for compressing and extracting features further involves generating, by at least one processor, at least one classifier for a defect of the object or an anomaly of the object, by applying the 3D data cube to a classifier algorithm. In some embodiments, the classifier algorithm is a supervised algorithm or while in others it is an unsupervised algorithm. In one or more embodiments, the method further involves reporting, by at least one processor, at least one classifier.

In at least one embodiment, the method further involves compressing, with at least one processor, at least one transformed signal to produce at least one compressed signal. In some embodiments, the method further involves decompressing, by at least one processor, at least one compressed signal to produce at least one decompressed signal. In one or more embodiments, the method further comprises regenerating, by at least one processor, the 3D data cube by using at least one decompressed signal.

In one or more embodiments, a system for compressing and extracting features comprises a transducer to transmit at least one ultrasound signal into an object at a plurality of different locations on the object. In at least one embodiment, each of the plurality of different locations is denoted by an x location and a y location. The system further comprises a receiver to receive at least one waveform response signal. Further, the system comprises at least one processor to generate a three-dimensional (3D) data cube with an X dimension, a Y dimension, and a time dimension. At least one waveform response signal is stored within the 3D data cube at the x location and the y location associated with the waveform response signal(s). At least one processor further transforms at least one waveform response signal of the 3D data cube to produce at least one transformed signal.

In at least one embodiment, at least one processor, to transform at least one waveform response signal, uses non-negative matrix factorization (NMF), total variation (TV), compressed sensing, and/or a method for deconvolution. In some embodiments, at least one processor further generates at least one classifier for a defect of the object or an anomaly of the object, by applying the 3D data cube to a classifier algorithm. In one or more embodiments, at least one processor further reports at least one classifier.

In one or more embodiments, at least one processor further compresses at least one transformed signal to produce at least one compressed signal. In at least one embodiment, at least one processor further decompresses at least one compressed signal to produce at least one decompressed signal. In some embodiments, at least one processor further regenerates the 3D data cube by using at least one decompressed signal.

In at least one embodiment, an apparatus for compressing and extracting features comprises a transducer to transmit at least one ultrasound signal into an object at a plurality of different locations on the object. In one or more embodiments, each of the plurality of different locations is denoted by an x location and a y location. The apparatus further comprises a receiver to receive at least one waveform response signal. Further, the apparatus comprises at least one processor to generate a three-dimensional (3D) data cube with an X dimension, a Y dimension, and a time dimension. At least one waveform response signal is stored within the 3D data cube at the x location and the y location associated with the waveform response signal(s). In some embodiments, the processor further transforms at least one waveform response signal of the 3D data cube to produce at least one transformed signal.

The features, functions, and advantages can be achieved independently in various embodiments of the present inventions or may be combined in yet other embodiments.

DRAWINGS

These and other features, aspects, and advantages of the present disclosure will become better understood with regard to the following description, appended claims, and accompanying drawings where:

FIG. 3 is a flow chart illustrating the disclosed method for compression and feature extraction from full waveform ultrasound data, in accordance with at least one embodiment of the present disclosure.

FIG. 4 is a formula for a physical model of an observed ultrasound waveform response signal.

FIG. 5 contains three graphs depicting the convolution of the components of an observed ultrasound waveform response signal.

DESCRIPTION

The methods and apparatus provide an operative system for compression and feature extraction from full waveform ultrasound data. The method and apparatus also provide a concept for compression of full waveform ultrasonic data during the scanning of materials, such as composite parts. In particular, the method and apparatus take advantage of the full waveform response signal by using the waveform response signal to form a three-dimensional (3D) data cube comprising two spatial dimensions and one time dimension.

Currently, for conventional ultrasonic scanning of parts (e.g., composite parts), during data collection, response data most commonly is stored as features (e.g., a C-scan) or as a sampled version of the full waveform. As a result, valuable aspects of the data can be lost. If the data needs to be revisited at a later date, archival of the full waveform data for updated/new analyses methods is not available. As composite structures become more complex (e.g., bonded structures and/or repaired structures), there is a need to have the full waveform data available for analysis.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1:
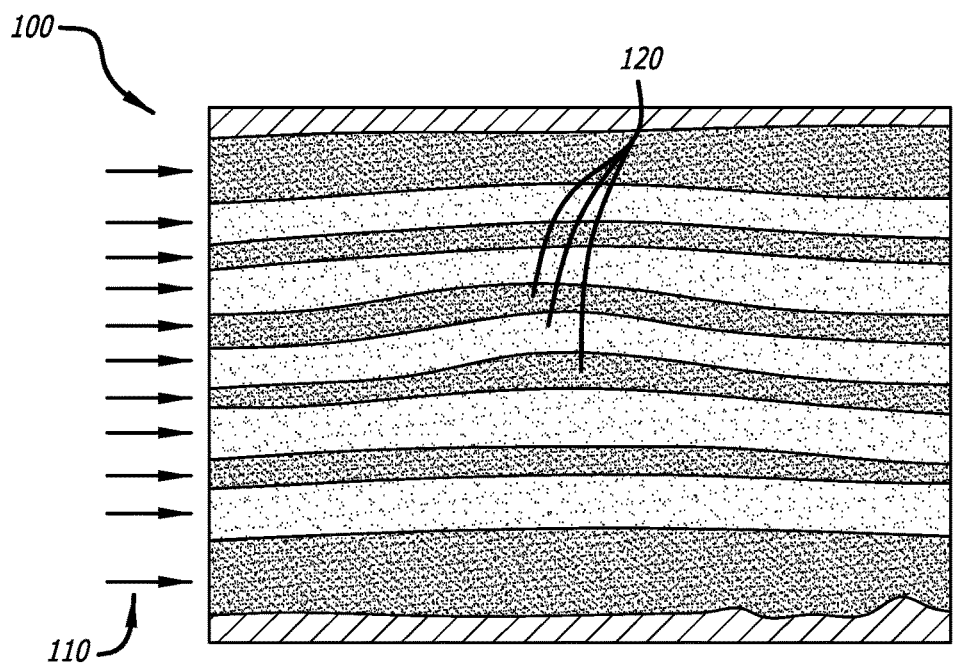
FIG. 1 is a diagram shown a cross-sectional side view of an exemplary piece of composite material that may be scanned by the disclosed system for compression and feature extraction from full waveform ultrasound data, in accordance with at least one embodiment of the present disclosure.

FIG. 1 is a diagram shown a cross-sectional side view of an exemplary piece of composite material 100 that may be scanned by the disclosed system for compression and feature extraction from full waveform ultrasound data, in accordance with at least one embodiment of the present disclosure. In this figure, this cross-sectional side view illustrates that the composite material 100 comprises a plurality of layers 110 of materials. In addition, as shown in this figure, the composite material 100 is shown to include a defect 120 in the form of several wrinkled (or non-linear) layers.

Figure 2:
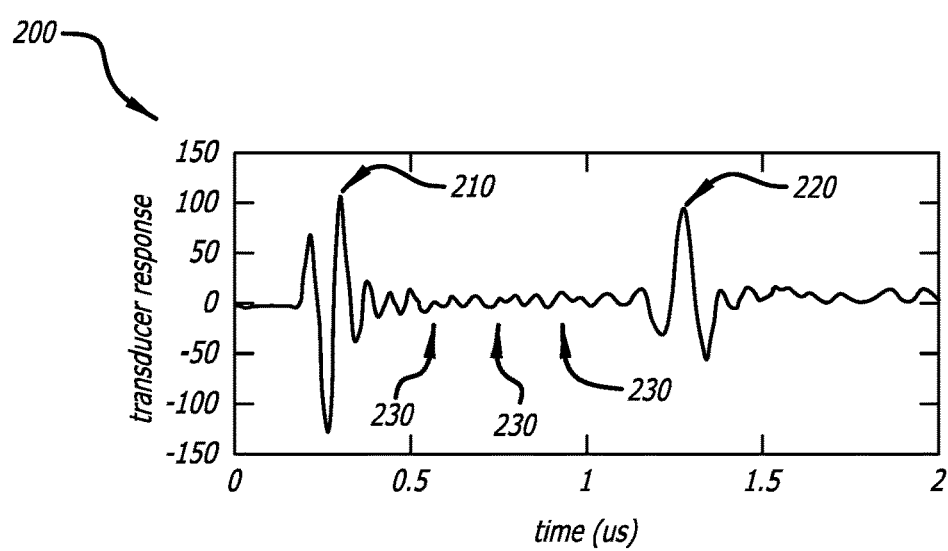
FIG. 2 is a graph showing an exemplary observed ultrasound waveform response signal.

FIG. 2 is a graph showing an exemplary observed ultrasound waveform response signal. Ultrasound inspection of parts involves sending out an ultrasonic wave, from a transducer, into the part at a particular location (x, y) on the surface of the part. A response signal, as shown in FIG. 2, is captured by the transducer. The response signal, as shown on the graph of FIG. 2, has units of time and amplitude. If the speed of sound in the part is known, then the time unit can be converted into a distance or depth into the part. Therefore, for an entire structure, if a waveform is recorded at every scan location, the result is a data cube that is a function of position (x, y), and time/depth.

For the response signal of FIG. 2, a part manufactured from a composite material, such as the composite material 100 shown in FIG. 1 is scanned by transmitting, with a transducer, an ultrasound signal into the part at a single x, y location. When the ultrasound signal reaches materials of different densities, the ultrasound signal is reflected back as a response signal. An example signal for a composite that is 0.05 inches thick is shown in FIG. 2. The response signal in FIG. 2 is shown to contain two large peaks 210, 220. The first large peak 210 of the response signal in FIG. 2 represents the ultrasound signal being reflected back when it reaches the top surface of the panel. And, the second large peak 220 represents the ultrasound signal being reflected back when it reaches the bottom surface of the panel. In addition, the small peaks 230 that lie in between the first peak 210 and the second peak 220 of the response signal represent the ultrasound signal being reflected back when it reaches each of the different layers 110 (refer to FIG. 1) of the composite material of the panel.

To store a complete waveform is very storage intensive. For example, to store the full waveform data for a 0.5 inch thick, 12 inch×12 inch panel, scanned at 0.08 inch increments at 100 megahertz (MHz), with an 8-bit resolution, will require 19.5 megabytes (MB) of storage (e.g., for nx=12 inches/0.08 inches=150, ny=150, and nt=0.5 inches*2/(0.11 inches/microsecond)=909; the memory required=nx*ny*nt). For a large airplane component, such as a wing skin, the amount of storage to store the data cube can be several gigabytes (GB). It is only in the recent years, with the advances in electronics and data storage, that it is even possible to record the full waveform data. Because of the large data storage requirements, particularly for portable ultrasound instruments used in the field, the current practice is to store what is known as a C-scan.

A C-scan is recorded by taking a single value from the waveform shown in FIG. 2, such as the maximum value, and storing only that single value. Typical values stored are the maximum amplitude of the waveform or the time between the waveform peaks. For the example of the 12 inch×12 inch×0.5 inch panel, recording only a single value of the waveform reduces the data storage requirement down to 22.0 kilobytes (kB). However, the rest of the information from the actual waveform is lost (i.e. once the C-scan is recorded, there is no way to recover the original waveform).

Another solution to the storage problem is to downsample the waveform. To keep the stored size of the waveforms to within a certain data size, the device will store every m number of points of the waveform (where the number m is chosen to limit the stored size accordingly), rather than store all the points of the waveform. Since the full waveform data contains valuable information for detecting defects within the structure, the currently used partial or selective storage schemes are likely not suitable for parts built by advanced materials, such as composite materials.

As previously mentioned, the current conventional methods (i.e. C-scan or down sampling) lose valuable scan information along the time domain. Defect recognition using the C-scan makes use of only the spatial information. Advanced defect detection methods making full use of the spatial and time information can be applied if the full waveform data is preserved. The system and method of the present disclosure addresses both the needs of storage of the full waveform and defect detection.

FIG. 3 is a flow chart illustrating the disclosed method 300 for compression and feature extraction from full waveform ultrasound data, in accordance with at least one embodiment of the present disclosure. At the start 305 of the method 300, ultrasound signals are sent by a transducer into an object at location x, y 310. Then, a receiver (e.g., which may be housed within the transducer) receives the full waveform response signal 315. A processor then determines whether more locations on the object need to be scanned 320. If the processor determines that more locations on the object need to be scanned, steps 310 and 315 are repeated.

Once the processor determines that no more locations on the object need to be scanned, the processor forms the three-dimensional (3D) data cube by using all of the received response signals 325. The 3D data cube comprises an X dimension, a Y dimension, and a time dimension. The received response signals are each stored within the 3D data cube at the x location (in the X dimension of the 3D data cube) and the y location (in the Y dimension of the 3D data cube) that corresponds to the received response signal's associated scanned x, y location. It should be noted that the term "cube" as used in the term "3D data cube" simply indicates that it is a 3D data set, which need not be in a true cube form. As such, the 3D data cube may or may not have equally sized sides.

After the 3D data cube is formed, the processor extracts feature vectors from the 3D data cube by performing a transform of each of the waveforms in the 3D data cube 330 to form a transformed 3D data cube. Various different methods may be employed by the disclosed method 300 to perform the transforms. Types of methods that may be employed include, but are not limited to, non-negative matrix factorization (NMF), total variation (TV), and deconvolution (e.g., deconvolution by using compressed sensing). It should be noted that NMF and TV methods are conventionally used for hyperspectral 3D imaging, but are not currently used for ultrasound imaging.

Then, after the processor extracts the feature vectors from the 3D data cube, the processor then generates classifiers for defects and/or anomalies in the object 335. In order to generate the classifiers for defects and/or anomalies of the object, the processer utilizes an algorithm that searches the 3D data cube for defects and/or anomalies in the object. The algorithm used by the processor may be a supervised algorithm or an unsupervised algorithm. A supervised algorithm has a baseline expected response waveform that it compares the received waveform to identify any defects and/or anomalies in the object. An unsupervised algorithm does not have a baseline expected response waveform to use as a comparison, but simply analyzes the data in the 3D data cube to identify any possible defects and/or anomalies in the object. In simplest case, a binary classifier can be generated to highlight the areas containing the defects and/or anomalies. After the processor generates the classifiers, the processor reports the defects and/or anomalies in the object 340. After the processor reports the defects and/or anomalies in the object, the method 300 ends 345.

Also, after the processor extracts the feature vectors from the 3D data cube, the processor performs compression of the transformed 3D data cube 350. In general, the compression ratio of a 3D data cube can be estimated by $L*(nx*ny+nt)/(nx*ny*nt)$, where L is the number of desired features (and $L \ll nt$); nx and ny are the number of samples in x and y; and nt is the number of time samples. For the example of the 12 inch×12 inch×0.5 inch panel, if the number of features (L) extracted is 100, the compression ratio is equal to 0.11, which equates to an 89 percent savings in required memory.

Once the processor performs compression of the transformed 3D data cube, the compressed 3D data cube is stored in storage 355. At a later time, or whenever desired, the compressed 3D data cube is decompressed 360 by the processor. Then, the processor regenerates the 3D data cube using the generated decompressed 3D data cube 365. After the processor regenerates the 3D data cube, the method 300 ends 345.

In other embodiments, one or more steps of the method may be collapsed into a single step and/or the steps may be performed in various different orders than the order depicted in FIG. 3. For example, the step (or process) of extracting feature vectors 330 and the step (or process) of performing compression 350 are performed together and, as such, those two steps are collapsed into a single step (or process).

In addition, it should be noted that in some embodiments when compressed sensing is utilized for the extracting of the feature vectors process 330, the compression process 350 is not performed after the extracting feature vectors process 330 as is shown in FIG. 3, but rather the compression process 350 is performed just after a full waveform response is received 315 for each location (i.e. the compression process 350 is performed in between the receive waveform step 315 and the determination of whether more locations are to be scanned step 320) to increase run-time efficiency.

For these embodiments, after all of the locations are scanned 310 and the waveforms for each location are received 315 and compressed 350, the extracting feature vectors process 330 is performed. As such, for these embodiments, a 3D data cube is not formed 325 from the received waveforms 315; but rather, after the feature vectors are extracted 330, the feature vectors are optionally stored in storage 355, decompressed 360, and then a 3D data cube can be generated 365.

As previously mentioned above, deconvolution (e.g., using the compressed sensing method for performing the deconvolution) is one method that may be used to transform of each of the response waveforms in the 3D data cube 330 to form a transformed 3D data cube (refer to step 330 of FIG. 3). The deconvolution of the response waveforms can help to more clearly identify the boundaries of the different layers of the composite object to aid in the detection of defects, such as wrinkles in the layers (refer to 120 of FIG. 1). FIG. 4 is a formula for a physical model of an observed ultrasound waveform response signal. In this formula, the observed signal is shown to be equal to the convolution of the pulse ($\Psi$) emitted from the transducer with the echoes from the object plus noise. When a deconvolution method is utilized to transform a response waveform (i.e. the observed signal), the result will be echoes plus noise.

FIG. 5 contains three graphs 500, 510, 520 depicting the convolution of the components 500, 510 of an observed ultrasound waveform response signal 520. In particular, graph 500 illustrates the pulse ($\Psi$) emitted from the transducer, graph 510 illustrates the echoes from the object plus noise, and graph 520 illustrates the observed waveform response signal. In this figure, the pulse ($\Psi$) emitted from the transducer 500 is shown to be convolved with the echoes plus noise 510 to form the observed waveform response signal 520.

In general, the scanned object may be selected from one of a mobile platform, a stationary platform, a land-based structure, an aquatic-based structure, a space-based structure, a surface ship, a tank, a personnel carrier, a train, a spacecraft, a space station, a satellite, a submarine, an automobile, a power plant, a bridge, a dam, a house, a manufacturing facility, a building, a fuselage, a composite part, a composite fuselage section, an engine housing, a wing, a horizontal stabilizer, a vertical stabilizer, a wall, a gas pipeline, a container, a person, a circuit board, a piece of luggage, and other suitable types of objects.

Although certain illustrative embodiments and methods have been disclosed herein, it can be apparent from the foregoing disclosure to those skilled in the art that variations and modifications of such embodiments and methods can be made without departing from the true spirit and scope of the art disclosed. Many other examples of the art disclosed exist, each differing from others in matters of detail only. Accordingly, it is intended that the art disclosed shall be limited only to the extent required by the appended claims and the rules and principles of applicable law.

We claim:

1. A method for obtaining and using ultrasound data from an object manufactured from a composite material comprising a plurality of layers to detect at least one defect in at least one of the layers, the method comprising:

scanning, by a transducer, at a plurality of different locations on the object;

transmitting, by the transducer, at least one ultrasound signal into the object at each of the plurality of different locations on the object, wherein each of the plurality of different locations is denoted by an x location and a y location;

receiving, by a receiver, at least one full waveform response signal from the object at each of the plurality of different locations on the object;

compressing, by at least one processor, each of the at least one full waveform response signal to generate at least one compressed full waveform;

determining, by the at least one processor, whether additional locations on the object need to be scanned, after the at least one processor compresses each of the at least one full waveform response signal;

generating, by the at least one processor, a compressed three-dimensional (3D) data cube with an X dimension, a Y dimension, and a time dimension, by using all of the compressed full waveforms, if no additional locations on the object need to be scanned based on the determining, wherein the compressed full waveforms are stored within the compressed 3D data cube at the x location and the y location associated with each of the compressed full waveforms;

generating, by the at least one processor, at least one classifier from the compressed 3D data cube; and detecting, by the at least one processor, the at least one defect in at least one of the layers of the composite material of the object by using at least one of the at least one classifier.

2. The method of claim 1, wherein the at least one processor uses compressed sensing for compressing the at least one full waveform response signal.

3. The method of claim 1, wherein the at least one classifier is generated by applying a classifier algorithm to the compressed 3D data cube.

4. The method of claim 3, wherein the classifier algorithm is one of a supervised algorithm or an unsupervised algorithm.

5. The method of claim 3, wherein the method further comprises reporting, by the at least one processor, the at least one classifier.

6. The method of claim 1, wherein the method further comprises decompressing, by the at least one processor, the compressed 3D data cube to produce a decompressed 3D data cube.

7. A system for obtaining and using ultrasound data from an object manufactured from a composite material comprising a plurality of layers to detect at least one defect in at least one of the layers, the system comprising:

a transducer configured to scan at a plurality of different locations on the object and to transmit at least one ultrasound signal into the object at each of the plurality of different locations on the object;

wherein each of the plurality of different locations is denoted by an x location and a y location;

a receiver configured to receive at least one full waveform response signal from the object at each of the plurality of different locations on the object;

at least one processor configured to compress each of the at least one full waveform response signal to, generate at least one compressed full waveform;

the at least one processor further configured to determine whether additional locations on the object need to be scanned, after the at least one processor compresses each of the at least one full waveform response signal;

the at least one processor further configured to generate a compressed three-dimensional (3D) data cube with an X dimension, a Y dimension, and a time dimension, by using all of the compressed full waveforms, after the at least one processor determines that no additional locations on the object need to be scanned, wherein the compressed full waveforms are stored within the compressed 3D data cube at the x location and the y location associated with each of the compressed full waveforms;

the at least one processor further configured to generate at least one classifier from the compressed 3D data cube; and the at least one processor further configured to detect the at least one defect in at least one of the layers of the composite material of the object by using at least one of the at least one classifier.

8. The system of claim 7, wherein the at least one processor uses compressed sensing for compressing the at least one full waveform response signal.

9. The system of claim 7, wherein the at least one classifier is generated by applying a classifier algorithm to the compressed 3D data cube.

10. The system of claim 9, wherein the classifier algorithm is one of a supervised algorithm or an unsupervised algorithm.

11. The system of claim 9, wherein the at least one processor is further to report the at least one classifier.

12. The system of claim 7, wherein the at least one processor is further to decompress the compressed 3D data cube to produce a decompressed 3D data cube.

13. An apparatus for obtaining and using ultrasound data from an object manufactured from a composite material comprising a plurality of layers to detect at least one defect in at least one of the layers, the apparatus comprising:

a transducer configured to scan at a plurality of different locations on the object and to transmit at least one ultrasound signal into the object at each of the plurality of different locations on the object;

wherein each of the plurality of different locations is denoted by an x location and a y location;

a receiver configured to receive at least one full waveform response signal from the object at each of the plurality of different locations on the object;

at least one processor configured to compress each of the at least one full waveform response signal to generate at least one compressed full waveform;

the at least one processor further configured to determine whether additional locations on the object need to be scanned, after the at least one processor compresses each of the at least one full waveform response signal;

the at least one processor further configured to generate a compressed three-dimensional (3D) data cube with an X dimension, a Y dimension, and a time dimension, by using all of the compressed full waveforms, after the at least one processor determines that no additional locations on the object need to be scanned, wherein the compressed full waveforms are stored within the compressed 3D data cube at the x location and the y location associated with each of the compressed full waveforms;

the at least one processor further configured to generate at least one classifier from the compressed 3D data cube; and the at least one processor further configured to detect the at least one defect in at least one of the layers of the composite material of the object by using at least one of the at least one classifier.

14. The apparatus of claim 13, wherein the at least one processor uses compressed sensing for compressing the at least one full waveform response signal.

15. The apparatus of claim 13, wherein the at least one classifier is generated by applying a classifier algorithm to the compressed 3D data cube.

16. The apparatus of claim 15, wherein the classifier algorithm is one of a supervised algorithm or an unsupervised algorithm.

17. A method for obtaining and using ultrasound data from an object manufactured from a composite material comprising a plurality of layers to detect at least one defect in at least one of the layers, the method comprising:

scanning, by a transducer, at a plurality of different locations on the object;

transmitting, by the transducer, at least one ultrasound signal into the object at each of the plurality of different locations on the object;

receiving, by a receiver, at least one full waveform response signal from the object at each of the plurality of different locations on the object;

compressing, by at least one processor, each of the at least one full waveform response signal to generate at least one compressed full waveform;

determining, by the at least one processor, whether additional locations on the object need to be scanned, after the at least one processor compresses each of the at least one full waveform response signal;

generating, by the at least one processor, a compressed three-dimensional (3D) data cube by using all of the compressed full waveforms, if no additional locations on the object need to be scanned based on the determining;

generating, by the at least one processor, at least one classifier from the compressed 3D data cube; and detecting, by the at least one processor, the at least one defect in at least one of the layers of the composite material of the object by using at least one of the at least one classifier.

18. The method of claim 17, wherein the at least one processor uses compressed sensing for compressing the at least one full waveform response signal.

19. The method of claim 17, wherein the method further comprises decompressing, by the at least one processor, the compressed 3D data cube to produce a decompressed 3D data cube.

20. The method of claim 17, wherein the at least one classifier is generated by applying a classifier algorithm to the compressed 3D data cube.

21. The method of claim 20, wherein the classifier algorithm is one of a supervised algorithm or an unsupervised algorithm.

* * * * *

UNITED STATES PATENT AND TRADEMARK OFFICE
CERTIFICATE OF CORRECTION

PATENT NO. : 10,203,243 B1
APPLICATION NO. : 13/660420
DATED : February 12, 2019
INVENTOR(S) : Yuan-Jye Wu and Hong H. Tat It is certified that error appears in the above-identified patent and that said Letters Patent is hereby corrected as shown below:

In the Claims

In Column 7, Line 58, remove ",".

Signed and Sealed this
Twenty-fifth Day of June, 2019

Andrei Iancu
*Director of the United States Patent and Trademark Office*